(12) United States Patent
Emanuel et al.

(10) Patent No.: US 8,992,887 B2
(45) Date of Patent: Mar. 31, 2015

(54) METHOD FOR MEDICAL IMAGING OF BODY CAVITIES

(75) Inventors: Mark Hans Emanuel, Aerdenhout (NL); Niek Exalto, Aerdenhout (NL)

(73) Assignee: GynaecologIQ B.V., Rotterdam (NL)

( * ) Notice: Subject to any disclaimer, the term of this patent is extended or adjusted under 35 U.S.C. 154(b) by 1763 days.

(21) Appl. No.: 11/632,364

(22) PCT Filed: Jul. 14, 2005

(86) PCT No.: PCT/NL2005/000507
§ 371 (c)(1), (2), (4) Date: Oct. 1, 2007

(87) PCT Pub. No.: WO2006/006861
PCT Pub. Date: Jan. 19, 2006

(65) Prior Publication Data
US 2008/0286206 A1 Nov. 20, 2008

(30) Foreign Application Priority Data
Jul. 15, 2004 (EP) .................................. 04077057

(51) Int. Cl.
*A61K 49/22* (2006.01)
*A61K 49/00* (2006.01)

(52) U.S. Cl.
CPC .................................. *A61K 49/226* (2013.01)
USPC .............................. 424/9.1; 424/1.11; 424/9.5

(58) Field of Classification Search
USPC ............. 424/4, 5, 709, 1.11, 9.1, 9.2; 514/54, 514/57, 717, 941–942; 600/441, 456, 458
See application file for complete search history.

(56) References Cited

U.S. PATENT DOCUMENTS

| | | | |
|---|---|---|---|
| 4,680,175 A * | 7/1987 | Estis et al. | 424/85.4 |
| 4,681,119 A | 7/1987 | Rasor et al. | |
| 4,985,233 A | 1/1991 | Klaveness et al. | |
| 5,352,434 A * | 10/1994 | Illig et al. | 424/9.411 |
| 6,280,702 B1 * | 8/2001 | Carter et al. | 424/9.1 |
| 7,727,155 B2 * | 6/2010 | De Ziegler | 600/458 |

FOREIGN PATENT DOCUMENTS

| | | |
|---|---|---|
| WO | 92/00707 A1 | 1/1992 |
| WO | 94/07417 A1 | 4/1994 |
| WO | 03/045308 A2 | 6/2003 |
| WO | 03/094710 A2 | 11/2003 |
| WO | WO-03/094710 * | 11/2003 |

OTHER PUBLICATIONS

Gloria Chi-Fishman and Barbaba Sonies, Effects of Systematic Bolus Viscosity and Volume Changes o Hyoid Movement Kinematics, Dysphagia, 1-17, 2002.*
MSD Sheet—1998.*

* cited by examiner

*Primary Examiner* — Michael G Hartley
*Assistant Examiner* — Jagadishwar Samala
(74) *Attorney, Agent, or Firm* — Gilberto M. Villacorta; Sunit Talapatra; Foley & Lardner LLP

(57) ABSTRACT

The present invention relates to an image enhancing composition for the enhancement of contrast in a body cavity, wherein the viscosity of the composition is between 2000 and 4000 mPa·sec. It also relates to a method for enhancing contrast of an image of a body cavity, which method involves introducing one single small aliquot of an image enhancing composition into the body cavity. In another aspect, the present invention provides a high contrast image of a body cavity obtained by the method of the invention, in particular a 3-dimensional high contrast image.

8 Claims, 2 Drawing Sheets

METHOD FOR MEDICAL IMAGING OF BODY CAVITIES

BACKGROUND OF THE INVENTION

1. Field of the invention

This invention relates to compositions and methods for medical imaging of the human or animal body. In particular to medical imaging with high contrast.

2. Description of the Related Art

Medical diagnostic imaging is widely used for the examination of body cavities. A prerequisite for the imaging of body cavities is the instillation of a fluid in order to obtain a fluid-filled cavity. In these fluid-filled cavities, the fluid has two functions (1) to open up the cavity from its "collapsed" state (distension) and (2) to enhance the contrast of the image of the body cavity. Conventionally, water or watery fluids are used for distension and contrast imaging. Sometimes, this is combined with the generation of bubbles, to further increase contrast. For example, U.S. Pat. No. 4,681,119 describes novel compositions and methods for generating microbubbles in a liquid-filled cavity for enhancing ultrasonic images of such cavities.

Since water easily leaks from the body cavity, it has to be replenished continuously during imaging. This is one of the big disadvantages of the use of water as a contrast medium during examination or imaging. This disadvantage may be solved partly by using liquid installation devices which reduce the leakage. For instance, a catheter equipped with an inflatable balloon may be used. However, this is not very convenient for the patient.

WO 03/094710 suggests a solid or semi-solid phase-shifting medium of pH 7.4 for providing contrast enhancement and/or distention of the subject body or organ cavity during imaging, radiographic visualisation or similar medical examinations. The medium is designed to have high, but undefined, viscosity initially and then to liquefy or lose viscosity after a period of time in order to facilitate easy removal of the medium from the body cavity. This phase-shifting medium includes polymers such as starches, and colloidal clays, such as bentonite and tragacanth, in order to achieve the phase shift. Disadvantage of such ingredients is that the additives, such as starches, will interfere with image formation.

WO 92/00707 describes an opthalmic gel suspension for dry eye application containing lightly cross-linked polymers of acrylic acid with a particle size of not more than 50 micrometer. These polymers are formulated with one or more opthalmic demulgents, such as cellulose derivatives, polivinyl alcohol or polyvinylpyrrolidone, or ophtalmic vasoconstrictors, and optionally with opthalmic adjuvants or additives, into gel suspensions. The opthalmic suspensions have a pH of about 6.6-8.0 and a viscosity of 500 to 4000 centipoise. Due to the acrylic acid polymers, these compositions will not be the preferred choice for imaging body cavities. In addition, the particles in these opthalmic gel suspension will interfere with image formation.

Therefore, there is a need for alternative contrast agents which do not easily leak from the body cavity during examination and which enable high quality images without jeopardising the safety of the patient.

SUMMARY OF THE INVENTION

It is an object of the present invention to provide an image enhancing composition for the enhancement of contrast in a body cavity, such as the uterine cavity, wherein the composition has a pH in the range of 5.5 to 7.5 and a viscosity in the range of 2000 to 4000 mPa·sec. when measured at room temperature. It is also an object of the present invention to provide a method for enhancing the contrast of an image of a body cavity, as well as to provide a high contrast image of a body cavity obtained by using said method.

Figure 1C:
FIGS. 1A-D
Figure 1D:
Figure 1A:
Figure 1B:
Figure 2:
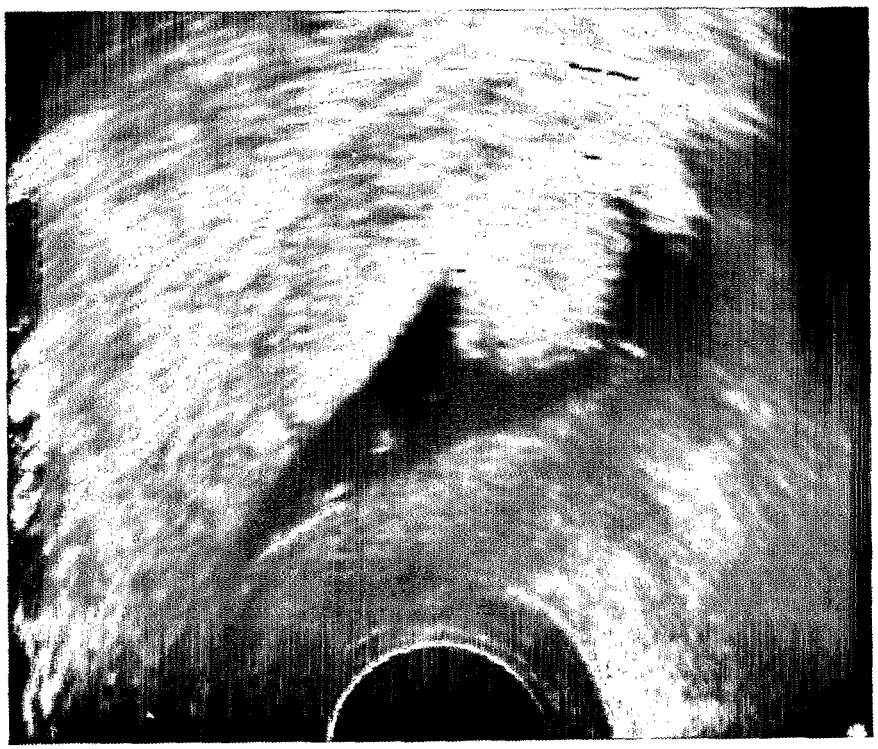

Illustrate a three dimensional picture of a uterus, wherein the picture was made using a gel composition according to the invention and a clear and sharp image without artifacts is obtained.

FIG. 2

Illustrates a two dimensional picture of a uterus, wherein the picture is made using conventional medium and three dimensional pictures are not possible with conventional medium because it would contain many artifacts due to a high flow of the medium.

DETAILED DESCRIPTION OF THE PREFERRED EMBODIMENTS

The present invention relates to an image enhancing composition for the enhancement of contrast in a body cavity, wherein the viscosity of the composition is between 2000 and 4000 mPa·sec.

One of the advantages of the image enhancing compositions of the invention is that they overcome the inconveniences and discomfort caused by saline infusions. With these state of the art saline infusions fluid leakage frequently occurs if a catheter is used, or pain is experienced due to pressure of a balloon catheter.

Another advantage is that only small aliquots of the compositions according to the invention are needed to achieve an optimal distension of a body cavity.

Due to a much smaller leakage velocity in comparison to saline, examination of the cavity is possible for several minutes, even after removal of the installation device.

Compositions of the invention have a viscosity of between 2000 and 4000 mPa·sec. as determined by standard viscosity determination methods, measured at room temperature and under atmospheric pressure. In one embodiment, the viscosity of the composition of the invention is between 2500 and 3500, preferably between 2700 and 3000 mPa·sec. More preferably, the viscosity of a composition of the invention is between 2800 and 2900 mPa·sec. when measured at room temperature. At body temperature the viscosity of a composition of the invention will be lower. Preferably, the viscosity will be between 2300 and 2500 mPa·sec. most preferably it will be between 2400 and 2500 mPa·sec. when measured at body temperature.

Image enhancing compositions of the invention may be used for all types of medical imaging, including X ray imaging, echography, magnetic resonance imaging, CT scanning and ultrasound imaging. Preferably, they are used for ultrasound imaging. More preferably, it is used for 3-dimensional ultrasound imaging.

As used herein, "image enhancement" refers to increasing the contrast of an image. The contrast enhancement may be either negative (black) or positive (white).

Typically, enhancement also involves distension of the body cavity of which an image is made. The compositions of the invention may be used for the imaging of any body cavity, including each part of the gastro-intestinal tract, such as the stomach, the colon. the duodenum; the bladder, the vagina. In a preferred embodiment, the body cavity is the uterine cavity.

Compositions of the invention should consist of substances which are safe for use in the human or animal body. They should be echo-lucent and the should therefore not contain particulate material, such as starch. Suitably, compositions of the invention are clear and do not contain particles, bubbles or protein, which will disturb the signal.

In one embodiment, the composition of the invention comprises a cellulose derivative, such as hydroxyethylcellulose or methylcellulose, in a buffer. Preferably, the composition comprises hydroxyethylcellulose. It is important that the composition contains so much of the cellulose derivative to achieve a viscosity of between 2000 and 4000 mPa·sec. as determined by standard viscosity determination methods, measured at room temperature and under atmospheric pressure, preferably between 2500 and 3500, or between 700 and 3000 mPa·sec. More preferably, enough to achieve a viscosity of between 2800 and 2900 mPa·sec. when measured at room temperature. At body temperature, a viscosity of between 2300 and 2500 mPa·sec., most preferably of between 2400 and 2500 mPa·sec. should be achieved.

The skilled person will understand that adjuvants, such as disinfectants or a local anaesthetic, may be added, for instance glycerine, lidocaine and chlorohexidine. In addition contrast enhancers may be added, such as iodine for X-ray imaging. However, in a preferred embodiment of the invention the composition consists substantially of a cellulose derivative, such as hydroxyethylcellulose or methylcellulose in a buffer, and no other adjuvants such as alcohol, polyvidone, lidacoine, or related compounds.

The pH value of the composition is between about 5.5 and about 7.5. Preferably, between about pH 6.0 and about 7.0, more preferably between about pH 6.3 and about 6.8.

In another aspect, the compositions of the invention may be used to manufacture an image enhancing medium for use in a medical imaging procedure. The composition may advantageously be used in 3-dimensional imaging procedures. In one embodiment, the compositions of the invention are used in 3-dimensional sonohysterography. In another aspect, the invention provides for the use of an image enhancing composition according to the invention for enhancing contrast of an image of a body cavity. The method comprises introducing one single small aliquot of a medium comprising the composition of the invention in the body cavity. The skilled person will understand that the amount which has to be administered or introduced will be dependent on the size of the body cavity which has to be imaged. Typically, about 1-about 10 ml will be enough for most body cavities. In one embodiment, about 3-about 5 ml of an image enhancing composition according to the invention is used for ultrasonic examination of the uterine cavity. Constant infusion of the composition is not necessary, which is a great advantage of the method of the present invention.

A medium comprising a compositions of the invention may be administered or introduced in a body cavity by methods known in the art and depending on the body cavity which is to be examined. For instance, for examination of the uterus, the composition is typically administered via an instillation device, such as a catheter.

In yet another aspect, the invention provides for high contrast images which are obtainable by using the compositions of the invention. Also encompassed in the invention, are high contrast 3-dimensional images. In particular, high contrast 3-dimensional images of the bladder, gastro-intestinal tract and the uterus. In a preferred embodiment, the invention is used for so-called virtual hysteroscopy. Three dimensional imaging requires a very stable and quiet filling of the cavity of interest, with a minimum amount of artefacts. The gel and method of the invention enables this.

EXAMPLE

This example demonstrates how the compositions and method of the invention may effectively and safely be used for sonohysterography.

The composition used for sonohysterography was a sterile, clear viscous gel containing hydroxyethylcellulose, glycerin, lidocaine (2% w/w) and chlorohexidine (0.05% w/w) buffered with acetic acid.

The composition was instilled using a cheap and easy to handle instillation device developed with a back-flow valve and flexible cervical adaptation, preventing leakage of the gel to the vagina. However, state of the art installation devices may be used instead.

The ultrasonic properties of the gel appeared comparable to saline in the first 120 patients. With only about 4 ml already an optimal distension could be achieved (range 2-10 ml). The gel could therefore be instilled from a normal 10 ml syringe fixed to the device and carefully flushed prior to the instillation preventing the introduction of air bubbles. Due to a much slower leakage velocity as compared to saline, ultrasonographic examination of the uterine cavity was possible for a long time even after removal of the instillation device. Only in a few cases a quick collapse of the uterine cavity was seen directly after removal of the device. This also illustrated that there was hardly any leakage of the gel through the Fallopian tubes. Installation of the gel was less painful as compared to the introduction of a balloon catheter. This shows that gel instillation is an alternative for saline infusion and can be used effectively and safe for sonohysterography. Gel instillation sonohysterography offers a more stable filling of the uterine cavity allowing detailed examination without inconveniences.

The invention claimed is:

1. A method of imaging a body cavity, comprising:
   (a) introducing into a body cavity an aliquot of echo-lucent image enhancing composition having a pH between 5.5 to 7.5 and a viscosity between 2000 to 4000 mPa·sec at room temperature wherein the composition consists essentially of hydroxyethylcellulose and/or methylcellulose, glycerin and a buffer; and
   (b) imaging the body cavity to produce an image.

2. The method according to claim 1, wherein the composition does not contain particulate material.

3. The method according to claim 1, wherein the composition is free of disinfectants and anaesthetics.

4. The method according to claim 1, wherein the imaging is 3-dimensional imaging.

5. The method according to claim 4, wherein the image is a high contrast 3-dimensional image.

6. The method according to claim 1, wherein the body cavity is a uterine cavity.

7. The method according to claim 1, wherein the imaging is ultra-sound imaging.

8. The method according to claim 1, wherein the imaging is sonohysterography.

* * * * *